United States Patent
Lee et al.

(10) Patent No.: US 10,485,823 B2
(45) Date of Patent: Nov. 26, 2019

(54) METHOD FOR TREATING CERVICAL INTRAEPITHELIAL NEOPLASIA USING POLY-GAMMA- GLUTAMIC ACID

(71) Applicant: BIOLEADERS CORPORATION, Gyeonggi-do (KR)

(72) Inventors: Il-Han Lee, Gyeonggi-do (KR); Seung Hoon Kim, Seoul (KR); Min Young Park, Daejeon (KR)

(73) Assignee: BIOLEADERS CORPORATION, Daejeon (KR)

( * ) Notice: Subject to any disclaimer, the term of this patent is extended or adjusted under 35 U.S.C. 154(b) by 0 days.

(21) Appl. No.: 15/132,218

(22) Filed: Apr. 18, 2016

(65) Prior Publication Data

US 2017/0296576 A1 Oct. 19, 2017

(30) Foreign Application Priority Data

Apr. 18, 2016 (KR) .................. 10-2016-0046947

(51) Int. Cl.
| | | |
|---|---|---|
| *A61K 31/785* | (2006.01) | |
| *A61K 47/10* | (2017.01) | |
| *A61K 47/16* | (2006.01) | |

(52) U.S. Cl.
CPC ............ *A61K 31/785* (2013.01); *A61K 47/10* (2013.01); *A61K 47/16* (2013.01)

(58) Field of Classification Search
None
See application file for complete search history.

(56) References Cited

U.S. PATENT DOCUMENTS

| | | | | |
|---|---|---|---|---|
| 2004/0138187 A1* | 7/2004 | Reading | .................. | A61K 31/58 514/169 |
| 2006/0234192 A1* | 10/2006 | Prescott | ............... | A61K 31/785 434/110 |
| 2010/0256050 A1* | 10/2010 | Sung | ..................... | A61K 31/785 514/3.7 |
| 2010/0256089 A1* | 10/2010 | Maguire | .............. | A61K 9/0031 514/54 |

FOREIGN PATENT DOCUMENTS

| | | |
|---|---|---|
| KR | 10-0475406 | 2/2005 |
| KR | 10-0496606 | 6/2005 |
| KR | 10-0496606 B1 | 6/2005 |
| KR | 10-0500796 | 7/2005 |
| KR | 10-0517114 | 9/2005 |
| KR | 10-0517114 B1 | 9/2005 |
| KR | 10-0656560 | 12/2005 |
| KR | 10-0656560 | 12/2006 |
| KR | 10-2012-0047491 A | 5/2012 |

OTHER PUBLICATIONS

Koo, Y.-J., et al., "Efficacy of Poly-Gamma-Glutamic Acid in Women with High-Risk Human Papillomavirus-Positive Vaginal Intraepithelial Neoplasia: an Observational Pilot Study", "Journal of Microbiology and Biotechnology", Apr. 23, 2015, pp. 1163-1169, vol. 25, No. 7.

Cho, H., et al., "Short-Term Clinical and Immunologic Effects of Poly-Gamma-Glutamic Acid (y-PGA) in Women with Cervical Intraepithelial Neoplasia 1 (CIN 1): A Multicenter, Randomized, Double Blind, Phase II Trial", "PLOS One", 2019, pp. 1-12.

* cited by examiner

*Primary Examiner* — David J Blanchard
*Assistant Examiner* — Sarah J Chickos
(74) *Attorney, Agent, or Firm* — Hultquist, PLLC; Steven J. Hultquist

(57) ABSTRACT

The present invention is directed to a method of treating cervical intraepithelial neoplasia by administering a composition containing poly-gamma-glutamic acid. According to the present invention, cervical intraepithelial neoplasia in unmarried women, pre-childbirth women, or women who do not want infertility, can be treated without concern about infertility.

3 Claims, 2 Drawing Sheets ns, cervical neoplasia is often unexpectedly recurred. Because cervical conization in unmarried women, pre-childbirth women, or women who do not want infertility, can cause sequelae such as abortion, premature birth, difficult pregnancy or infertility, immunotherapy with drugs is preferable.

METHOD FOR TREATING CERVICAL INTRAEPITHELIAL NEOPLASIA USING POLY-GAMMA- GLUTAMIC ACID

TECHNICAL FIELD

The present invention relates to a method for treating cervical intraepithelial neoplasia using poly-gamma-glutamic acid, and more particularly, to a method for treating cervical intraepithelial neoplasia, comprising administering to a patient with cervical intraepithelial neoplasia a composition comprising poly-gamma-glutamic acid, aspartame and a pharmaceutically acceptable excipient.

BACKGROUND ART

Poly-gamma-glutamic acid (PGA) is a viscous polymer consisting of D and L-glutamic acids polymerized through gamma-glutamyl bonds. It is produced from *Bacillus* sp. strains isolated from Chungkookjang (Korean traditional fermented soybean food prepared using rice-straw), Natto (Japanese traditional fermented soybean food), Kinema (Nepalese traditional fermented soybean food), etc. PGA that is produced from *Bacillus* sp. strains is an edible, water-soluble, anionic, and biodegradable polymeric substance. It is known that the PGA can be used as a raw material for moisture absorbers, moisturizers and cosmetics, and as a raw material for the preparation of naturally degradable plastics by using the synthesis of ester derivatives.

The present inventors have obtained a patent (Korean Patent No. 10-500796) directed to a method of producing poly-gamma-glutamic acid using a *Bacillus subtilis* Chungkookjang strain that is a salt-tolerant strain producing high-molecular-weight poly-gamma-glutamic acid. Also, the present inventors have obtained patents (Korean Patent Nos. 10-496606, 10-517114 and 10-475406) directed to an anticancer composition, an immune adjuvant and an immune enhancer, which contain poly-gamma-glutamic acid (PGA). In recent years, a patent directed to an anticoagulant and antithrombotic composition containing poly-gamma-glutamic acid has been granted (Korean Patent No. 10-0656560).

An immune adjuvant or enhancer containing poly-gamma-glutamic acid has been used together with an antibody for the purpose of increasing antibody immunity. In this regard, poly-gamma-glutamic acid alone did not serve to increase immunity.

Meanwhile, cervical neoplasia is the beginning stage of cervical cancer in which cervical epithelial cells are transformed into dysplastic cells by infection with human papillomavirus. As gynaecological examination has been widely conducted, cervical neoplasia, which is the beginning stage of cervical cancer, has recently been diagnosed, but appropriate treatment of cervical neoplasia with drugs has not been performed. Cervical neoplasia is divided into three stages in accordance with the type of symptoms. In the case of stage 1 cervical neoplasia, it is the best choice to watch the progress of the disease. However, if stage 2 or stage 3 cervical neoplasia is diagnosed, surgery should be taken into consideration together with diagnosis, because a further advanced lesion may exist.

Particularly, if cervical neoplasia is diagnosed as stage 3, a lesion more severe than stage 3 may exist, and thus surgical procedures such as cervical conization may be performed. Cervical conization is a medical procedure in which a cone-shaped tissue is excised from the cervix. Since an infected site is removed, it appears that guaranteed removal of HPV virus is possible; however, cervical neoplasia is often unexpectedly recurred. Because cervical conization in unmarried women, pre-childbirth women, or women who do not want infertility, can cause sequelae such as abortion, premature birth, difficult pregnancy or infertility, immunotherapy with drugs is preferable.

Accordingly, the present inventors have made extensive efforts to develop a method capable of treating cervical intraepithelial neoplasia without surgery, and as a result, have found that, when a composition containing poly-gamma-glutamic acid is administered to a patient with cervical intraepithelial neoplasia, it causes no side effects and exhibits a high therapeutic effect with high stability, thereby completing the present invention.

DISCLOSURE OF INVENTION

Technical Problem

It is an object of the present invention to provide a method for treating cervical intraepithelial neoplasia using a composition containing poly-gamma-glutamic acid as an active ingredient.

Technical Solution

To achieve the above object, the present invention provides a method for treating cervical intraepithelial neoplasia, comprising administering to a patient with cervical intraepithelial neoplasia a composition containing poly-gamma-glutamic acid, aspartame and a pharmaceutically acceptable excipient.

Advantageous Effects

According to the present invention, cervical intraepithelial neoplasia can be treated without surgery, and thus cervical intraepithelial neoplasia in unmarried women, pre-childbirth women, or women who do not want infertility, can be treated without concern about infertility.

BEST MODE FOR CARRYING OUT THE INVENTION

Figure 1:
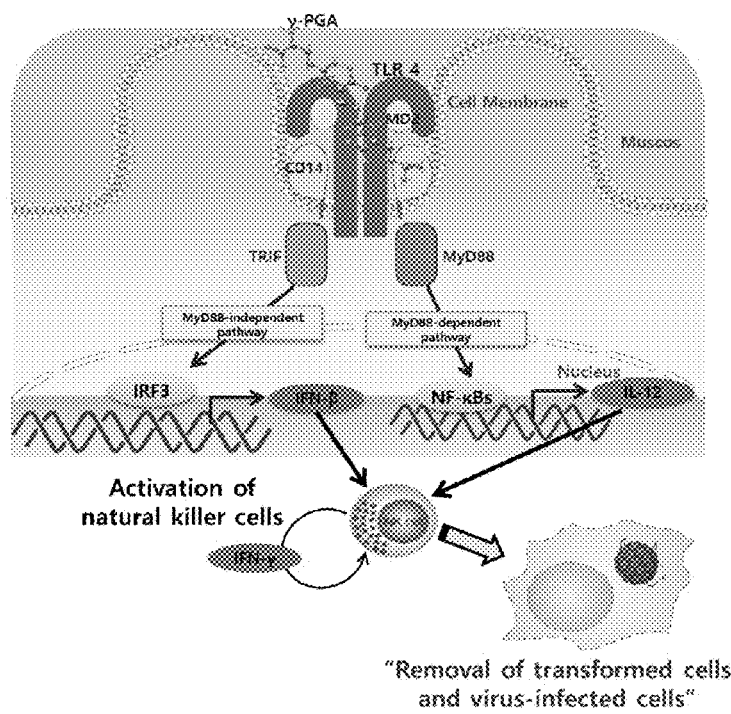
FIG. 1 schematically shows the mechanism by which cervical intraepithelial neoplasia is treated using poly-gamma-glutamic acid.
Figure 2:
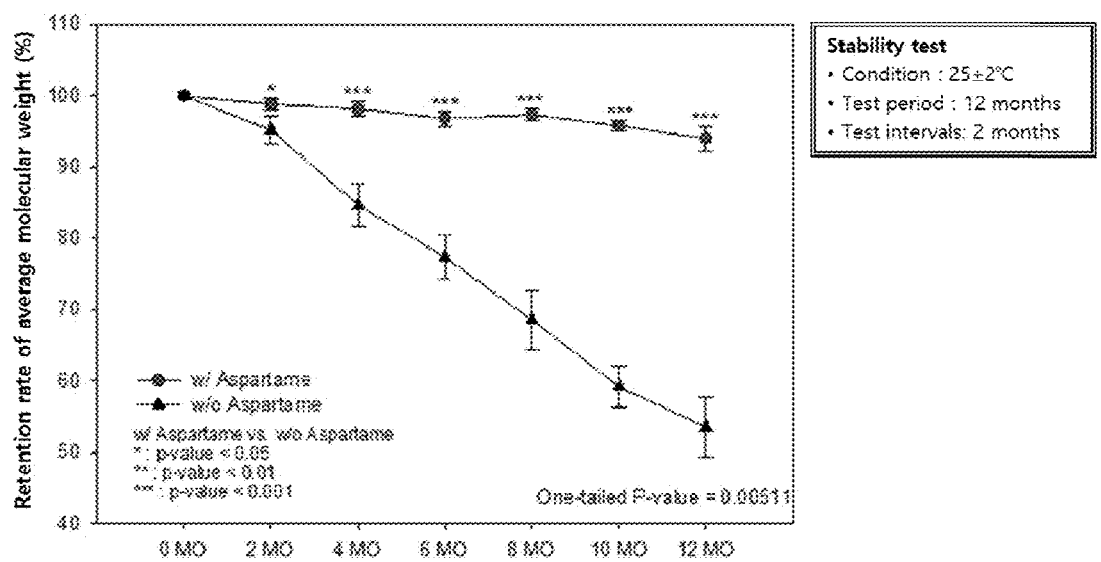
FIG. 2 is a graph showing the retention rate of the average molecular weight of poly-gamma-glutamic acid by addition of aspartame.

In the present invention, in order to verify whether poly-gamma-glutamic acid (known as an immune adjuvant), a biopolymer produced by *Bacillus subtilis*, is effective for the treatment of cervical intraepithelial neoplasia, a formulation containing poly-gamma-glutamic acid was administered to patients diagnosed as having cervical intraepithelial neoplasia for 4 weeks, thereby confirming the therapeutic effect of poly-gamma-glutamic acid on cervical intraepithelial neoplasia.

Thus, the present invention is directed to a method for treating cervical intraepithelial neoplasia, comprising administering to a patient with cervical intraepithelial neoplasia a composition containing poly-gamma-glutamic acid, aspartame and a pharmaceutically acceptable excipient.

In the present invention, the aspartame may be contained in an amount of 0.001-1 part by weight based on 100 parts by weight of the poly-gamma-glutamic acid.

In the present invention, the excipient may include a material selected from the group consisting of stevioside, methyl paraoxybenzoate, and propyl paraoxybenzoate.

The composition according to the present invention may contain, based on 100 parts by weight of poly-gamma-glutamic acid, 0.001-0.1 parts by weight of aspartame, 0.005-0.03 parts by weight of stevioside, 0.2-0.01 parts by weight of methyl paraoxybenzoate, and 0.05-0.005 parts by weight of propyl paraoxybenzoate.

In the present invention, a solvent for the composition may be a mixture of ethanol and water.

In an example of the present invention, a composition comprising 93 g of poly-gamma-glutamic acid, 30 mg of aspartame, 10 mg of stevioside, 80 mg of paraoxybenzoate, 20 mg of propyl paraoxybenzoate, 3.86 g of purified water, and 3 g of ethanol was administered to a patient with cervical intraepithelial neoplasia, thereby confirming the therapeutic effect of poly-gamma-glutamic acid on cervical intraepithelial neoplasia.

Using a test group administered with poly-gamma-glutamic acid plus aspartame and a control group administered with poly-gamma-glutamic acid alone, the rate of decrease in the molecular weight of the poly-gamma-glutamic acid was independently measured three times at two-month intervals for 12 months. As a result, it was shown that the molecular weight in the test group was not reduced as compared to that in the control group and was also statistically significant. It was found that a poly-gamma-glutamic acid composition with high stability can be prepared by adding aspartame.

Cervical intraepithelial neoplasia is a condition in which cell transformation has occurred due to HPV infection. It can be regarded as a pre-carcinogenic stage. This cervical intraepithelial neoplasia begins at the normal epithelial cells of the cervical surface, transforms all the epithelial cells gradually with the progress of the disease, and is highly likely to develop into invasive cancer when reaching the basal membrane.

Cervical intraepithelial neoplasia is divided into three stages and is diagnosed by histological examination.

Currently, a standard therapy for cervical intraepithelial neoplasia does not exist, and resection is performed to excise all the infected tissues while the progression of the disease is observed. This resection causes serious side effects such as infertility or discharging blood in fertile women. When cervical intraepithelial neoplasia reaches the invasive stage, it is diagnosed as cervical cancer, and resection and anti-cancer therapy are performed, and when the extent of the invasion is severe, potential metastasis to other parts should be checked.

Poly-gamma-glutamic acid transduces signals through TLR4 and the accessory proteins MD2 and CD14 essential for TLR4 signaling. The transduced signals increase the expression of the transcriptional factors NK-κB and IRF3 essential for cytokine expression through the MyD88 pathway that is the typical signaling pathway of TLR4 and through the TRIF pathway. The transcriptional factors with increased expression act on the respective cytokine promoter regions to induce the production of cytokines, including IFN-β, IL-12 and the like. The produced IFN-β and IL-12 induce activation of natural killer cells, and the activated natural killer cells remove transformed cells and virus-infected cells from the cervix.

The carrier used in the pharmaceutical composition of the present invention comprises pharmaceutically acceptable carriers, adjuvants and vehicles in the pharmaceutical field, which are as a whole called "pharmaceutically acceptable carriers." The pharmaceutically acceptable carriers useful in the pharmaceutical composition of the present invention, include, but not limited to, ion exchange resin, alumina, aluminum stearate, lecithin, serum proteins (e.g., human serum albumin), buffering agents (e.g., sodium phosphate, glycine, sorbic acid, potassium sorbate, partial glyceride mixtures of saturated vegetable fatty acids), water, salts or electrolytes (e.g., protamine sulfate, disodium hydrophosphate, potassium hydrophoshate, sodium chloride, and zinc salts), colloidal silica, magnesium trisilicate, polyvinylpyrrolidone, cellulose-based substrates, polyethylene glycol, sodium carboxymethylcellulose, polyarylate, waxes, polyethylene-polyoxypropylene-block copolymers, polyethylene glycol, and wool fat.

The pharmaceutical composition according to the present invention can be administered by various routes, including, but not limited to, oral, intravenous, intramuscular, intra-arterial, intramedullary, intradural, intracardial, transdermal, subcutaneous, intraperitoneal, intranasal, gastrointestinal, local, sublingual and rectal routes.

Preferably, the pharmaceutical composition of the present invention is administered orally or parenterally. The term "parenteral", as used herein, includes subcutaneous, intradermal, intravenous, intramuscular, intraarticular, intrasynovial, intrasternal, intrathecal, intralesional, and intracranial injection or infusion techniques.

The pharmaceutical composition of the present invention may be in the form of a sterile injectable preparation, such as a sterile injectable aqueous or oily suspension. Such suspensions may be formulated according to the methods known in the art, using suitable dispersing or wetting agents (e.g., Tween 80) and suspending agents. The sterile injectable preparations may also be a sterile injectable solution or suspension in a non-toxic parenterally-acceptable diluent or solvent, such as a solution in 1,3-butanediol. The acceptable vehicles and solvents include mannitol, water, Ringer's solution and isotonic sodium chloride solution. In addition, sterile inert oils may conventionally be employed as a solvent or suspending medium. For this purpose, any non-volatile oil having low irritation may be employed, including synthetic mono- or di-glycerides. In addition, fatty acids, such as oleic acid and glyceride derivatives thereof, may be used in the preparation of injectable preparations, like pharmaceutically acceptable natural oils (e.g., olive oil or castor oil), and particularly, polyoxyethylated derivatives thereof.

The pharmaceutical composition of the present invention may be orally administered in any orally acceptable dosage form including, but not limited to, capsules, tablets, and aqueous suspensions and solutions. In the case of tablets for oral use, commonly used carriers include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical composition of the present invention may also be administered in the form of suppositories for rectal administration. The composition can be prepared by mixing the compound of the present invention with a suitable non-irritating excipient that is solid at room temperature but liquid at rectal temperature. Such excipients include, but are not limited to, cocoa butter, beeswax and polyethylene glycols.

Oral administration of the pharmaceutical composition according to the present invention is especially useful when the desired treatment involves areas or organs readily accessible by topical application. For application topically to the skin, the pharmaceutical composition should be formulated with a suitable ointment containing the active component suspended or dissolved in a carrier. Carriers for topical administration of the compound of the present invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical composition of the present invention may also be topically applied to the lower intestinal tract by rectal suppository formulation or in a suitable enema formulation. Topically-transdermal patches are also included in the present invention.

The pharmaceutical composition of the present invention may be administered by nasal aerosol or inhalation. Such a composition is prepared according to techniques well-known in the art of pharmaceutical formulation and may be prepared as a solution in saline, employing benzyl alcohol or other suitable preservatives, absorption promoters to enhance bioavailability, fluorocarbons, and/or other solubilizing or dispersing agents known in the art.

The compound of the present invention may be used in combination with either conventional anti-inflammatory agents or with matrix metalloprotease inhibitors, lipoxygenase inhibitors and antagonists of cytokines other than IL-10.

The compound of the present invention can also be administered in combination with immunomodulators (e.g., bropirimine, anti-human alpha-interferon antibody, IL-2, GM-CSF, methionine enkephalin, interferon-alpha, diethyldithiocarbamate, tumor necrosis factor, naltrexone and rEPO) or with prostaglandins to prevent or combat IL-1-mediated disease symptoms such as inflammation. When the compound of the present invention is administered in combination with other agents, they may be administered sequentially or concurrently to the patient. Alternatively, the pharmaceutical composition according to the present invention may comprise another therapeutic or prophylactic agent.

The pharmaceutical composition of the present invention may be used for the treatment of infectious diseases, particularly diseases associated with viral infection. Diseases/conditions that can be treated or prevented by the pharmaceutical composition of the present invention include, but are not limited to, tuberculosis, gonorrhoea, typhoid, meningitis, osteomyelitis, meningococcal infections, endometritis, peritonitis, pyelonephritis, pharyngitis, septic arthritis, cellulitis, epiglottitis, salpingitis, otitis media, a cold, influenza, enteritis, dysentery and gastroenteritis.

As used herein, the term "therapeutically effective amount" refers to a dosage level of 100-5,000 mg/patient/day, preferably 500-3,000 mg/patient/day, which is used for the treatments of the above-described symptoms.

However, it will be understood that a particular effective amount for any particular patient will vary depending upon a variety of factors, including the activity of the specific compound employed, the age, body weight, general health status, sex, diet, administration time and route, excretion rate, drug combination, and the severity of the disease to be prevented or treated. The pharmaceutical composition according to the present invention may be formulated as tablets, sugar-coated tablets, capsules, liquids, gels, syrups, slurries, or suspensions.

The composition of the present invention may be injected into muscle cells or other cells in muscle tissue or cells of viscera within the abdominal cavity.

In a preferred embodiment, a pharmaceutical composition for oral administration can be prepared by mixing the active ingredient with a solid excipient and may also be prepared in a granular form in order to prepare tablets or sugar-coated tablets. Suitable excipients include sugars such as lactose, sucrose, mannitol and sorbitol, carbohydrates such as starch from corn, flour, rice, potato or other plants, celluloses such as methyl cellulose, hydroxypropylmethyl-cellulose or sodium carboxymethylcellulose, gums, including arabic gum and tragacanth gum, protein fillers, including gelatin and collagen, etc. If necessary, disintegrating agents or solubilizing agents such as cross-linked polyvinylpyrrolidone, agar or alginic acid or a salt thereof, such as sodium alginate, may be added.

In case of parenteral administration, in a preferred embodiment, the pharmaceutical composition according to the present invention may be prepared in the form of an aqueous solution. Preferably, a physically appropriate buffer, such as Hank's solution, Ringer's solution, or physically buffered saline, may be used. Water-soluble injectable suspensions may include a substrate that can increase the viscosity of the suspension, such as sodium carboxymethyl cellulose, sorbitol, or dextran. Additionally, suspensions of the active ingredient may be prepared as oily injection suspensions. Suitable lipophilic solvents or vehicles include fatty oils such as sesame oil, or synthetic fatty acid esters, such as ethyl oleate or triglycerides, or liposomes. Polycationic amino polymers may also be used as carriers. The suspension may optionally contain stabilizers or agents to increase the solubility of the compound and to allow for more concentrated solutions.

A monoclonal antibody in the pharmaceutical composition is adsorbed onto a glass vessel such as a vial and a syringe, and is also unstable, and it easily loses its activity by various physical chemical factors, for example, heat, pH and humidity. Thus, a stabilizer, a pH adjusting agent, a buffer, a solubilizer, a surfactant, etc. are added to formulate the monoclonal antibody into stable form. Examples of the stabilizer include amino acids such as glycine and alanine, saccharides such as dextran 40 and mannose, sugar alcohols such as sorbitol, mannitol and xyltol, which may also be used in combination of two or more. These stabilizers are preferably added in an amount corresponding to 0.01-100 times (particularly 0.1-10 times) the weight of the antibody. Addition of these stabilizers can enhance the storage stability of liquid formulations or lyophilized formulations. Examples of the buffer include phosphate buffer, citrate buffer, etc. The buffer adjusts the pH of aqueous solution after re-dissolution of liquid formulations or lyophilized formulations and contributes to the stability and solubility of the antibody. The buffer is preferably added in an amount of, for example, 1-10 mM based on the amount of a liquid formulation or lyophilized formulation after re-dissolution. Examples of the surfactant include polysorbate 20, pulluronic F-68, polyethyleneglycol, etc. Preferably, polysorbate 80 is used, and these surfactants may be used in combination of two or more.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Comparison of Effect Between Composition Containing Poly-Gamma-Glutamic Acid Only and Formulation of the Present Invention Poly-gamma-glutamic acid having an average molecular weight of 2,000-3,500 kDa was prepared as a control. In addition, a test group adding aspartame (0.03%) to the poly-gamma-glutamic acid identical to that used in the control group was prepared. To prepare a standard calibration curve, a polyacrylamide standard corresponding to each average molecular weight was prepared. The average molecular weight of each group was measured by gel permeation chromatography. A standard calibration curve was prepared using the calibration information obtained by measuring the prepared standard. Then, the calibration information obtained by loading the prepared sample into gel permeation chromatography was substituted into the standard calibration curve, thereby determining the average molecular weight of the test sample. Using the above test method, the rate of decrease in the molecular weight of the poly-gamma-glutamic acid was independently measured three times at 2-month intervals for 12 hours.

As a result, it was shown that the molecular weight in the test group was not reduced as compared to that in the control group and was also statistically significant. In addition, it was found that a poly-gamma-glutamic acid composition with high stability can be prepared by the addition of aspartame.

Example 2

Evaluation of Therapeutic Effect in Cervical Intraepithelial Neoplasia Patients

On fertile women with cervical intraepithelial neoplasia (CIN1), poly-gamma-glutamic acid was administered orally, and a multicenter, randomized, double-blind, placebo-controlled parallel, phase-2b clinical trial was performed to evaluate the reduction of cervical intraepithelial neoplasia and the safety of poly-gamma-glutamic acid.

For 178 fertile women with cervical intraepithelial neoplasia (CIN1), 100 ml of the therapeutic composition containing poly-gamma-glutamic acid as shown in Table 1 was administered to each of 92 fertile women, once each day, before retiring for 4 weeks, and a placebo containing no poly-gamma-glutamic acid was administered to 86 fertile women as a control group in the same manner as described above.

TABLE 1

| | Contents | Component per 100 ml |
|---|---|---|
| Main component | poly-gamma-glutamic acid solution | 93 g |
| Sweetener | aspartame | 30 mg |
| | stevioside | 10 mg |
| Preservative | methyl paraoxybenzoate | 80 mg |
| | propyl paraoxybenzoate | 20 mg |
| Solvent | Purified water | 3.68 g |
| | Ethanol | 3 g |

For evaluation of the therapeutic effect, at 3 months after administration of the composition, the cervical intraepithelial tissue was biopsied and stained, and then the dysplastic stage of the cells was determined by pathologists (Colposcopic biopsy). The stage of dysplasia was divided into CINI, CINII, CINIII and SCC (squamous cell carcinoma), and the degree of cell dysplasia was evaluated in comparison with that before administration of the composition.

As the therapeutic effect of the composition according to the present invention, the change of the tissue cells from the dysplastic cells (CINI) to normal cells was confirmed based on pathological findings.

To evaluate primary effectiveness, the cure rate at 12 weeks after drug administration compared to before drug administration (baseline (within −4 weeks)) was compared between the test group (PGA) and the control group (Placebo). Herein, the cure is defined as a change from the CIN I stage to normal, based on the final determination on a clinical subject as determined by an independent evaluation committee.

The results of the primary effectiveness evaluation performed in this Example are shown in Table 2 below.

TABLE 2

| | | placebo group | | PGA group | | P-value* |
|---|---|---|---|---|---|---|
| Including indeterminate | ITT1** | N = 86 | | N = 92 | | |
| | Normal regression | 26 | 30.23% | 42 | 45.65% | 0.0247 |
| | ITT2** | N = 96 | | N = 99 | | |
| | Normal regression | 26 | 27.08% | 42 | 42.42% | 0.0178 |
| | PP | N = 70 | | N = 80 | | |
| | Normal regression | 22 | 31.43% | 37 | 46.25% | 0.0455 |

*One-tailed exact test with a significant level of 5% (Jung's method (2008));
**ITT1 excludes the case having no biopsy material;
ITT2 includes the case having no biopsy material and is replaced with CIN I measured in screening based on LOCF.

The results of analysis of the ITT groups indicated that a difference of 16 people was shown and also statistically significant, and the results of analysis of the PP groups indicated that a difference of 15 people was shown and statistically significantly.

The ITT (intent-to-treat) analysis is an analysis method in which all randomly assigned subjects are regarded as the originally assigned group regardless of the treatment that they actually received. In this method, even when the test for randomly assigned patients is discontinued, the evaluation of the patients is continued, and the evaluation results for these patients are included in analysis. It can be said to be a conservative approach method.

On the contrary, the PP (Per Protocol) analysis can be said to be a method in which data for subjects who stop the test for various reasons are excluded from analysis.

In the phase-2 clinical study conducted to confirm the increase in cure rate (immunotherapeutic effect) compared to the natural cure rate of cervical intraepithelial neoplasia and safety, when poly-gamma-glutamic acid (γ-PGA) was administered to fertile women with cervical intraepithelial neoplasia (CIN I), the therapeutic effect (cure rate) in the test group was statistically significantly higher than that in the placebo group.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating cervical intraepithelial neoplasia, comprising administering to a patient with cervical intraepithelial neoplasia a pharmaceutical composition comprising poly-gamma-glutamic acid having an average molecular weight of 2,000-3,500 kDa, aspartame, stevioside, methyl paraoxybenzoate, and propyl paraoxybenzoate, wherein the pharmaceutical composition comprises based on 100 parts by weight of poly-gamma-glutamic acid, 0.001-1 part by weight of aspartame, 0.005-0.03 parts by weight of stevioside, 0.2-0.01 parts by weight of methyl paraoxybenzoate, and 0.05-0.005 parts by weight of propyl paraoxybenzoate.

2. The method of claim 1, wherein pharmaceutical composition further comprises a solvent comprising a mixture of ethanol and water.

3. The method of claim 1, wherein said administering comprises parenteral administration.

* * * * *

UNITED STATES PATENT AND TRADEMARK OFFICE
CERTIFICATE OF CORRECTION

PATENT NO. : 10,485,823 B2
APPLICATION NO. : 15/132218
DATED : November 26, 2019
INVENTOR(S) : Lee et al.

Page 1 of 1

It is certified that error appears in the above-identified patent and that said Letters Patent is hereby corrected as shown below:

In the Specification

Column 1, Line 4, following the title "METHOD FOR TREATING CERVICAL INTRAEPITHELIAL NEOPLASIA USING POLY-GAMMA-GLUTAMIC ACID", and before the heading "TECHNICAL FIELD", insert the following heading and paragraph:

--CROSS-REFERENCE TO RELATED APPLICATION
This application claims priority under the provisions of 35 U.S.C. §119 of Korean Patent Application No. 10-2016-0046947 filed April 18, 2016. The disclosure of such Korean priority patent application is hereby incorporated herein by reference in its entirety, for all purposes.--

Signed and Sealed this
Seventh Day of January, 2020

Andrei Iancu
*Director of the United States Patent and Trademark Office*